United States Patent
Keohane et al.

(10) Patent No.: US 11,803,919 B2
(45) Date of Patent: Oct. 31, 2023

(54) DYNAMIC COLLECTION AND DISTRIBUTION OF CONTEXTUAL DATA

(71) Applicant: International Business Machines Corporation, Armonk, NY (US)

(72) Inventors: Susann Keohane, Austin, TX (US); David Wright, Riverview, MI (US)

(73) Assignee: International Business Machines Corporation, Armonk, NY (US)

( * ) Notice: Subject to any disclaimer, the term of this patent is extended or adjusted under 35 U.S.C. 154(b) by 559 days.

(21) Appl. No.: 15/832,365

(22) Filed: Dec. 5, 2017

(65) Prior Publication Data
US 2019/0172157 A1 Jun. 6, 2019

(51) Int. Cl.
*G06Q 50/00* (2012.01)
*G06N 3/08* (2023.01)
(Continued)

(52) U.S. Cl.
CPC ........... *G06Q 50/01* (2013.01); *A61B 5/0022* (2013.01); *A61B 5/1118* (2013.01);
(Continued)

(58) Field of Classification Search
CPC .............. G01C 21/12; G06K 9/00785; G06K 9/00288; G06K 9/00302; G06K 9/00335; G06K 9/00885; G06K 9/00342; G06K 2009/00328; G06K 9/00221; G06K 9/00261; G06K 9/00268; G06K 9/6201;
(Continued)

(56) References Cited

U.S. PATENT DOCUMENTS 8,861,804 B1 * 10/2014 Johnson ............... G06F 16/587
382/218
8,892,391 B2 11/2014 Tu et al.
(Continued)

FOREIGN PATENT DOCUMENTS

CA 2812011 C 8/2016
WO WO-2012127484 A1 * 9/2012 ............ G06Q 30/02
WO 2016054290 A1 4/2016

OTHER PUBLICATIONS

Santos et al., "Providing user context for mobile and social networking applications", Jun. 2010, ScienceDirect, vol. 6, Issue 3, pp. 324-341; https://www.sciencedirect.com/science/article/pii/S1574119210000052 (Year: 2010) (Year: 2010).*
(Continued)

*Primary Examiner* — Lynda Jasmin
*Assistant Examiner* — Kimberly L Evans
(74) *Attorney, Agent, or Firm* — Amin, Turocy & Watson, LLP

(57) ABSTRACT

Techniques for automatically collecting data and updating social media profiles based on sensor data are discussed herein. A system can comprise an activity identification component that based on sensor data received by the activity identification component, identifies an activity associated with an entity of a mobile device, resulting in an identified activity. Additionally, the system can comprise an updating component that based on the identified activity, updates a social media profile associated with the activity with activity data related to the identified activity.

18 Claims, 10 Drawing Sheets

(51) Int. Cl.
| | |
|---|---|
| *A61B 5/11* | (2006.01) |
| *H04L 67/306* | (2022.01) |
| *A61B 5/00* | (2006.01) |
| *G06V 40/10* | (2022.01) |
| *H04L 67/50* | (2022.01) |

(52) U.S. Cl.
CPC ............. *A61B 5/6898* (2013.01); *G06N 3/08* (2013.01); *G06V 40/10* (2022.01); *H04L 67/306* (2013.01); *H04L 67/535* (2022.05)

(58) Field of Classification Search
CPC .......... G06N 20/00; G06N 3/08; G06N 7/005; G06N 20/10; H04L 67/22; H04L 67/306; H04L 63/083; H04L 63/0861; H04L 63/0876; H04L 63/107; H04L 67/38; H04L 67/535; G06F 3/011; G06F 16/2365; G06F 16/2379; G06F 16/285; G06F 21/316; G06F 21/32; G06F 30/20; G06F 40/186; G06F 1/163; G06F 19/3481; G06F 3/016; G06F 3/0482; G06F 3/04883; G06F 19/3418; G06F 16/24575; G06F 3/012; G06F 3/017; G06F 3/0304; G06F 2216/03; G06F 9/54; G06F 16/2465; G06F 16/48; G06F 16/9535; G06F 17/30038; G06F 17/30539; G06F 17/30867; G06Q 10/063112; G06Q 10/06393; G06Q 10/06398; G06Q 10/067; G06Q 10/105; G06Q 30/018; G06Q 50/2057; G06Q 50/01; G06Q 30/0207; G06Q 30/0241; G06Q 20/00; G06Q 20/0453; G06Q 30/0201; H04N 5/77; A61B 5/1118; A61B 5/6898; G06V 40/23; G16H 40/67; H04W 4/21
USPC ...... 705/1.1, 329, 2, 319; 701/532; 702/141, 702/127, 187, 181; 600/301, 1; 700/174; 463/7; 362/118; 340/573.1; 345/573.1; 434/236; 382/218
See application file for complete search history.

(56) References Cited

U.S. PATENT DOCUMENTS

| | | | |
|---|---|---|---|
| 9,032,306 B2 | 5/2015 | Wang et al. | |
| 9,361,005 B2 | 6/2016 | Wheatley et al. | |
| 9,386,052 B2 | 7/2016 | Ownbey et al. | |
| 9,420,015 B2 | 8/2016 | Cherry et al. | |
| 9,472,080 B1* | 10/2016 | Guo | G08B 5/223 340/539 |
| 9,497,593 B2 | 11/2016 | Marti et al. | |
| 9,497,594 B2 | 11/2016 | Xie et al. | |
| 9,501,745 B2 | 11/2016 | Nitz et al. | |
| 2006/0033625 A1* | 2/2006 | Johnson | G06Q 40/08 705/2 |
| 2011/0106418 A1* | 5/2011 | van der Merwe | G01C 21/12 701/532 |
| 2012/0124176 A1 | 5/2012 | Curtis et al. | |
| 2012/0310587 A1* | 12/2012 | Tu | G01D 1/16 702/181 |
| 2012/0326873 A1* | 12/2012 | Utter, II | G06F 3/016 340/573.1 |
| 2013/0203475 A1* | 8/2013 | Kil | G16H 20/30 463/7 |
| 2013/0280682 A1* | 10/2013 | Levine | A61B 3/112 434/236 |
| 2014/0101611 A1 | 4/2014 | Lang et al. | |
| 2014/0129942 A1 | 5/2014 | Rathod | |
| 2014/0228649 A1* | 8/2014 | Rayner | A61B 5/1118 600/301 |
| 2015/0142689 A1* | 5/2015 | Squires | G01C 22/00 705/329 |
| 2016/0005001 A1* | 1/2016 | Muhammedali | G06Q 50/01 705/319 |
| 2016/0034634 A9* | 2/2016 | Hong | A61B 5/112 702/19 |
| 2017/0094450 A1* | 3/2017 | Tu | A61B 5/02438 702/141 |
| 2017/0140041 A1* | 5/2017 | Dotan-Cohen | G06Q 10/101 702/187 |
| 2017/0259115 A1* | 9/2017 | Hall | A63B 24/0062 345/573.1 |
| 2017/0374414 A1* | 12/2017 | Knox | H04N 21/44218 700/174 |
| 2019/0163831 A1* | 5/2019 | Anders | G06F 16/2465 702/127 |
| 2019/0163973 A1* | 5/2019 | Keohane | G06V 10/764 706/12 |
| 2020/0260287 A1* | 8/2020 | Hendel | G06N 5/04 726/1 |

OTHER PUBLICATIONS

Lane et al., "A Survey of Mobile Phone Sensing," Ad Hoc and Sensor Networks, IEEE Communications Magazine, Sep. 2010, pp. 140-150, IEEE, 11 pages.

Anonymously; "Proximity Based Activity Management Utilizing P2P, Geotagging and Location Awareness," PCOM000207904D, Jun. 16, 2011, 5 pages.

Santos, et al.; "Providing User Context for Mobile and Social Networking Applications," Pervasive and Mobile Computing, Jan. 12, 2010, 25 pages.

Miluzzo et al., "CenceMe—Injecting Sensing Presence into Social Networking Applications," Second European Conference on Smart Sensing and Context (EuroSSC 2007), Lecture Notes in Computer Science 4793, 2007, pp. 1-28, Springer, 28 pages.

Lockhart et al., "Applications of Mobile Activity Recognition," The 14th International Conference on Ubiquitous Computing (Ubicomp 2012), Sep. 2012, ACM, 5 pages.

* cited by examiner

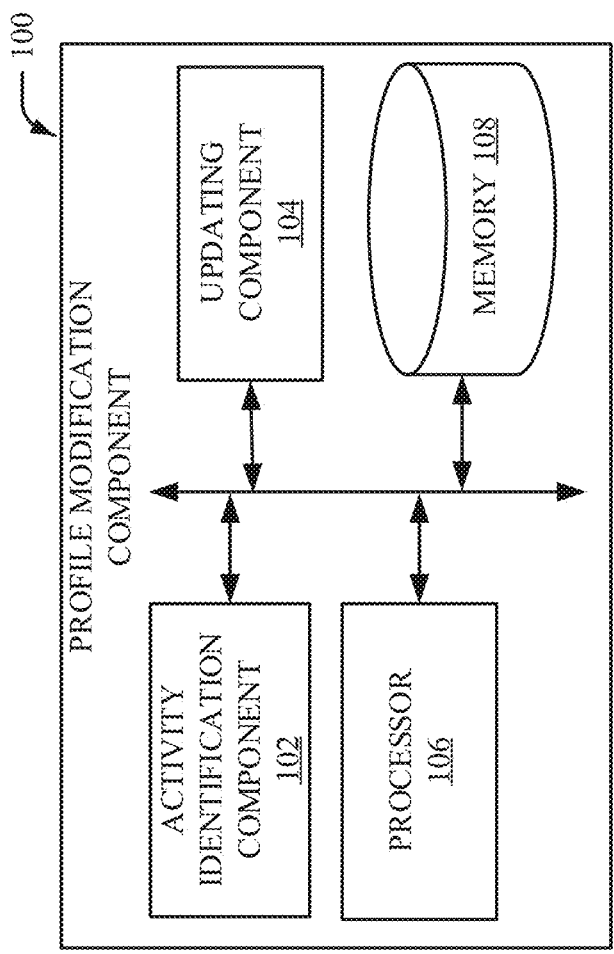
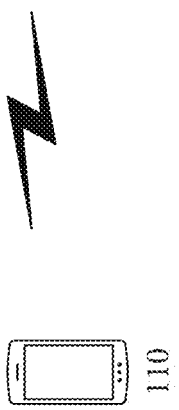
FIG. 1

DYNAMIC COLLECTION AND DISTRIBUTION OF CONTEXTUAL DATA

TECHNICAL FIELD

The subject disclosure relates to dynamic collection and distribution of contextual data.

SUMMARY

The following presents a summary to provide a basic understanding of one or more embodiments of the disclosure. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate automatically collecting and updating social media profiles based on sensor data are described.

According to an embodiment, a system can comprise a memory that stores computer executable components, and a processor that executes the computer executable components stored in the memory. The computer executable components of the system can comprise an activity identification component that, based on sensor data received by the activity identification component, identifies an activity associated with an entity of a mobile device, resulting in an identified activity. The computer executable components of the system can also comprise an updating component that, based on the identified activity, updates a social media profile associated with the activity with activity data related to the identified activity.

According to another embodiment, a computer program product that facilitates automated profile updates can comprise a computer readable storage medium having program instructions embodied therewith. The program instructions can be executable by a processor and the processor can identify an activity associated with an entity of a mobile device based on sensor data received by an activity identification component, resulting in an identified activity. The program instructions can also be executable to update, by the processor, a social media profile associated with the activity with activity data related to the identified activity based on the identified activity.

According to yet another embodiment, a computer-implemented method is provided. The computer-implemented method can comprise identifying, by a device operatively coupled to a processor, an activity associated with an entity of a mobile device based on sensor data received by an activity identification component resulting in an identified activity. The computer-implemented method can also comprise, updating, by the device, a social media profile associated with the activity with activity data related to the identified activity based on the identified activity.

According to yet another embodiment, a system can comprise a memory that stores computer executable components, and a processor that executes the computer executable components stored in the memory. The computer executable components of the system can comprise a collection component that, collects activity data associated with an activity of an entity from one or more sensors, wherein the one or more sensors are biometric sensors operable to sense the activity based on one or more biometric indicators associated with the entity. The computer executable components of the system can also comprise a neural network component that, based on the activity data, trains an automated profile updating system to determine the activity in the absence of the activity data, and updates a social media profile of the entity in accordance with the activity in the absence of the activity data.

According to yet another embodiment, a computer program product facilitates automated profile updates can comprise a computer readable storage medium having program instructions embodied therewith. The program instructions can be executable by a processor and the processor can collect activity data associated with an activity of an entity from one or more sensors, wherein the one or more sensors are biometric sensors operable to sense the activity based on one or more biometric indicators associated with the entity. The program instructions can also be executable to train an automated profile updating system to determine the activity in the absence of the activity data based on the activity data. Additionally, the program instructions can also be executable to update a social media profile of the entity in accordance with the activity in the absence of the activity data In some embodiments, one or more of the above elements described in connection with the systems, computer-implemented methods and/or computer program programs can be embodied in different forms such as a computer-implemented method, a computer program product, or a system.

DESCRIPTION OF THE DRAWINGS

FIG. 1 illustrates a block diagram of an example, non-limiting system that facilitates automatically collecting data and updating social media profiles based on sensor data in accordance with one or more embodiments described herein.

DETAILED DESCRIPTION

Figure 2:
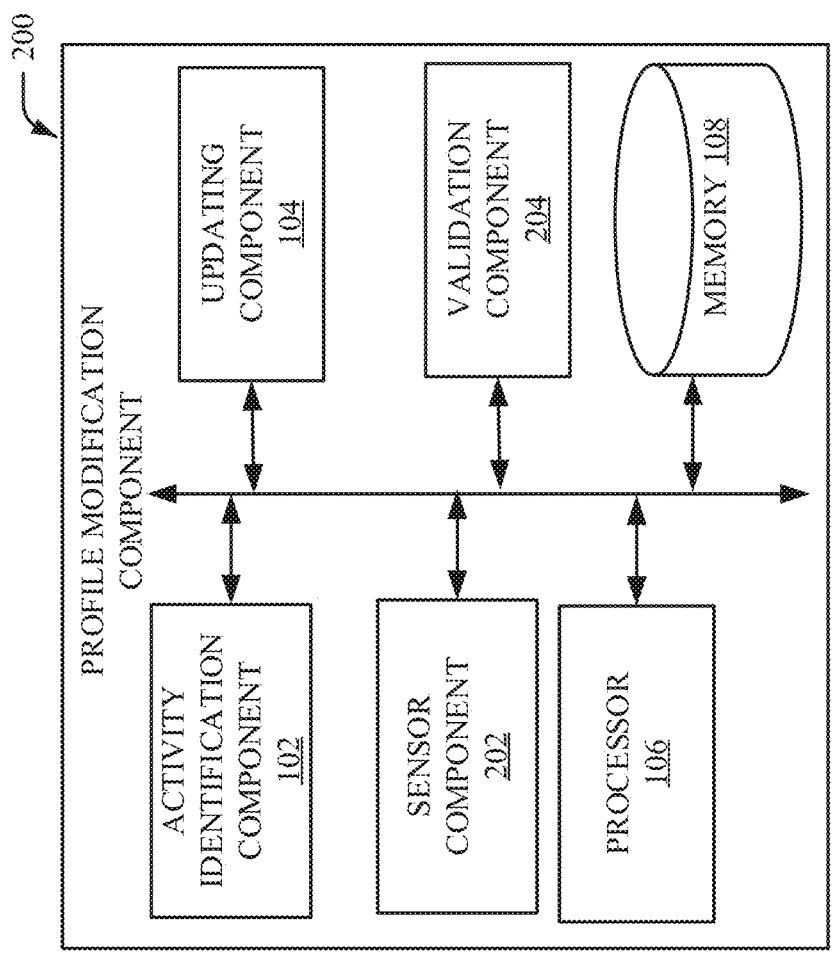
FIG. 2 illustrates a block diagram of an example, non-limiting system that facilitates automatically collecting data and updating social media profiles based on sensor data in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Internet of things (IOT) sensors and other sensors can be used to automatically update social media platforms. Thus, capturing the context of an entity's routines from sensor data can be useful for updating social media profiles associated with the entity. For example, specific events attended by multiple entities can be crowd sourced and curated to update a social media profile associated with one of the entities in real-time or near real-time. In some scenarios an entity may not be able to properly operate their mobile device to update their social media profile, however, by using the crowd sourced data, the entity can procure data related to the entity without accessing their mobile device. The entity can also monitor and validate the data prior to the data being uploaded to the entity's social media profile.

The system can use existing technologies to detect and identify nearby entities and/or devices via a wireless fidelity (Wi-Fi) network, Bluetooth, or future communication protocols not now known. Consequently, the system can monitor and analyze a nearby entity's social media feed and learn, from curated content, by using existing photo albums comprising entities, location data, time data, etc. Additionally, the system can create an entry based on friend's post or new post criteria related to another entity. For instance, the system can automatically fill in fields comprising who, what, when, and where details of an entity's actions. Additionally, based on an entity's content preferences (e.g., time, social media platform, conflicts, etc.) the system can determine what is not acceptable to be posted and/or prompt the entity for validation if the system cannot decide what is not acceptable to be posted.

One or more embodiments described herein can automatically collect data and update social media profiles based on sensor data. One or more embodiments described herein include systems, computer-implemented methods, apparatus, and computer program products that facilitate automatically collecting data and updating social media profiles based on sensor data.

FIG. 1 illustrates a block diagram of an example, non-limiting system that facilitates automatically collecting data and updating social media profiles based on sensor data in accordance with one or more embodiments described herein.

In various embodiments, the profile modification component 100 can be associated with or included in a data analytics system, a data processing system, a graph analytics system, a graph processing system, a big data system, a social network system, a speech recognition system, an image recognition system, a graphical modeling system, a bioinformatics system, a data compression system, an artificial intelligence system, an authentication system, a syntactic pattern recognition system, a medical system, a health monitoring system, a network system, a computer network system, a communication system, a router system, a server system or the like.

In one embodiment, the profile modification component 100 can perform an activity identification and profile updates. The profile modification component 100 can comprise several subcomponents including, but not limited to an activity identification component 102, an updating component 104, a processor 106, and a memory 108 that can bi-directionally communicate with each other. It should also be noted that in alternative embodiments that other components including, but not limited to the sub-components, the processor 106, and/or the memory 108, can be external to the profile modification component 100.

Aspects of the processor 106 can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described by the profile modification component 100. In an aspect, the profile modification component 100 can also include the memory 108 that stores computer executable components and instructions.

The profile modification component 100 can be employed to use hardware and/or software to solve problems that are highly technical in nature (e.g., automated profile updates, crowd sourcing, curating data, analyzing multiple data sets from multiple devices simultaneously, etc.), that are not abstract and that cannot be performed as a set of mental acts by a human due to the processing capabilities needed to facilitate automatically collecting data and updating social media profiles, for example. Further, some of the processes performed may be performed by a specialized computer for carrying out defined tasks related to memory operations. For example, a specialized computer can be employed to carry out tasks related to automatically collecting data and updating social media profiles or the like.

In the embodiment, as shown in FIG. 1, the profile modification component 100 can comprise the activity identification component 102 and the updating component 104, which can be electrically and/or communicatively coupled to one another in various embodiments. As shown in FIG. 1, the activity identification component can be configured to receive sensor data from one or more sensors and/or mobile devices. For instance, a mobile device 110 can take a picture of the entity running and send the picture to the profile modification component 100. The picture can then be received by the activity identification component 102, which can then identify an activity (e.g., running) that the entity is engaging in. In addition to the picture, sensors that are operable to receive data associated with the entity, can send sensor data to the activity identification component 102. Thus, the sensor data can also be used in determining the activity that the entity is engaging in.

For example, a heart monitor sensor, which can monitor a heart rate of the entity can send heart rate data to the activity identification component 102, wherein the heart rate data is indicative of the heart rate of the entity. Thus, the activity identification component 102 can combine the picture data and the heart rate data (e.g., indicating an elevated heart rate) to conclude that the entity is currently running. The sensor data can be received from the entity's mobile device and/or other mobile devices associated with other entities. It should be noted that any type of sensor can be used, and that sensors can include, but are not limited to: optical sensors, heart rate sensors, gyroscopes, accelerometers, facial recognitions sensors, global positioning system (GPS) sensors, microphones, audio sensors, light sensors, infrared sensors, radio frequency identification (RFID) sensors, etc. The sensor data can also be stored in a data store (not shown) for real-time use and/or future use as indicated with regards to a neural network below.

The updating component 104 can be configured to update a social media profile, associated with the entity, based on data received from the activity identification component 102. For example, now referencing the aforementioned running example, the social media profile of the entity can be updated with data indicating that the entity is running and/or has recently been on a run. The picture taken by the mobile device 110 can also be used to update the social media profile of the entity and/or the heart rate of the entity can be posted to the social media profile of the entity. Alternatively, simple text data can be used to update the entity's social media profile. For example, the text data can say, "entity is currently on a run", without the inclusion of the picture or the heart rate data. Thus, the profile modification component 100 can be configured to allow the entity to select which data can be automatically posted (e.g., the picture, the heart rate data, and/or the conclusion that the entity is running based on the data received from the activity identification component 102) to the social media profile. Additional examples of data selectivity are discussed below with regards to a validation component 204 of FIG. 2.

FIG. 2 illustrates a block diagram of an example, non-limiting system that facilitates automatically collecting data and updating social media profiles based on sensor data in accordance with one or more embodiments described herein. Repetitive description of like elements employed in other embodiments described herein is omitted for sake of brevity.

The profile modification component 200 can comprise one or more sensors via a sensor component 202 and the profile modification component 200 can comprise a validation component 204. The sensor component 202 can comprise various sensors operative to sense data associated with the entity. For example, if the profile modification component 200 is located within a mobile device, then the sensors of the mobile device (e.g., GPS, gyroscope, light sensor, etc.) can be used as the sensors of the sensor component 202. The sensors of the sensor component 202 can add another layer of granularity to the data received from external sensors to the profile modification component 200. Consequently, the more sensors that are used to confirm an activity, via the activity identification component 102, the higher the probability that the activity identification component 102 accurately identifies the activity. Additionally, the sensor component 202 can store previously curated sensor data for use in assisting the activity identification component 102 in identifying an activity.

The validation component 204 can automatically validate an activity and/or prompt the entity to confirm whether an activity is correct and/or whether the entity would like for the entity's social media profile to be updated with the data. For example, the entity can receive an update from the activity identification component 102 that the activity identification component 102 has determined that the entity is running based on the heart rate sensor. However, the entity may want to qualify the activity as jogging. Consequently, the entity can update the profile modification component 200 by inputting qualifying data that the heart rate sensor data should be qualified as jogging and not running Based on this information, the validation component 204 can confirm to the entity that the validation component will send the sensor data and the qualification of jogging to the updating component 104 to update the social media profile of the entity. Thus, the qualifying data can be used as baseline data thereafter to delineate jogging from running the next time heart rate sensor data is used to identify an activity.

Figure 3:
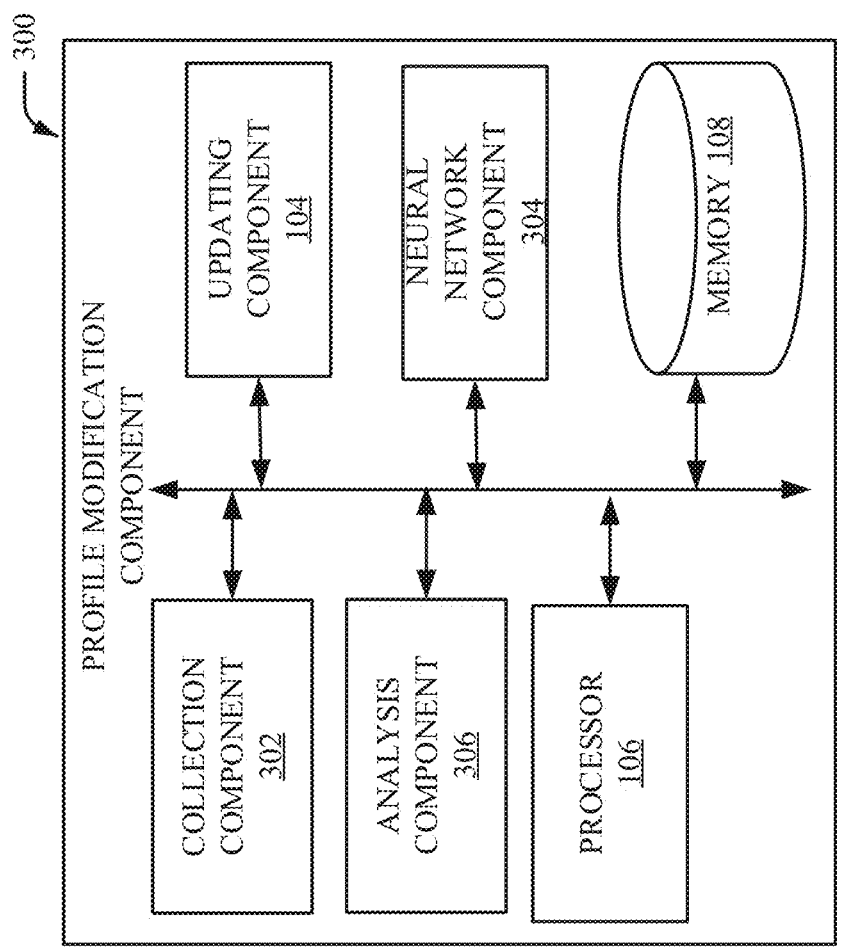
FIG. 3 illustrates a block diagram of an example, non-limiting system that facilitates automatically collecting data and updating social media profiles based on sensor data in accordance with one or more embodiments described herein.

FIG. 3 illustrates a block diagram of an example, non-limiting system that facilitates automatically collecting data and updating social media profiles based on sensor data in accordance with one or more embodiments described herein. Repetitive description of like elements employed in other embodiments described herein is omitted for sake of brevity.

FIG. 3 depicts the profile modification component 300 comprising a collection component 302, a neural network component 304, an analysis component 306, a processor 106 and a memory 108, which can be electrically and/or communicatively coupled to one another in various embodiments. The collection component 302 can receive and store relevant data from external sensors and its surroundings. The collection component can also partition and/or tag the received data based on where it came from. If the profile modification component 300 has received multiple data inputs from an originating source (e.g., a specific mobile device, a biometric sensor, etc.), then the data inputs can all be labeled as being received from the originating source. For example, biometric data from a biometric sensor can indicate that an entity has an elevated blood pressure. Based on the indication that the entity has an elevated blood pressure (and possibly other factors as well), the analysis component 306 can determine that the entity is engaging in a particular activity (e.g., swimming) The analysis component 306 can base its determination off inputs received from the entity, routine actions of the entity, multiple sensor data received from the collection component 302, etc. Furthermore, the analysis component 306 can compare its current determination to a determination generated by the neural network component 304 based on previous activity data from previous iterations.

It should also be noted that an AI component can facilitate automating one or more features in accordance with the disclosed aspects. A memory and a processor as well as other components can include functionality with regard to the figures. The disclosed aspects in connection with collecting data and updating social media profiles can employ various AI-based schemes for carrying out various aspects thereof. For example, a process for detecting one or more trigger events, determining an activity as a result of the one or more trigger events, and updating a social media profile, and so forth, can be facilitated with an example automatic classifier system and process. In another example, a process for penalizing a sensor while preferring another sensor, based on accuracy in determining the activity, can be facilitated with the example automatic classifier system and process.

An example classifier can be a function that maps an input attribute vector, x=(x1, x2, x3, x4, xn), to a confidence that the input belongs to a class, that is, f(x)=confidence(class). Such classification can employ a probabilistic and/or statistical-based analysis (e.g., factoring into the analysis utilities and costs) to prognose or infer an action that can be automatically performed (e.g., updating a social media profile). For example, a specific sensor can be identified as being more relevant than others for determining a specific activity. Therefore, sensor data from that specific sensor can be weighted more heavily by the neural network component 304 in relation to determining the activity. For instance, velocity sensor data of a velocity sensor can be weighted more heavily as being relevant to a bicycle moving than a heart rate sensor of an entity when it comes to determining whether the entity is riding the bicycle. Since an entity's elevated heart rate can be attributed to other physical activities such as running, jogging, swimming, etc., the velocity sensor data indicating that the bicycle is moving at ten miles per hours is a better indicator to predict that the entity is bicycling even if both sensors are utilized in making the determination. Thus, the neural network component 304 and the analysis component 306 can utilize the tagged and/or partitioned data (e.g., via the collection component 302) to determine a probability associated with the activity determination being correct. Additionally, the neural network component 304 can be configured to generate activity identification data where there is an absence or lack of data received from the sensors. Thus, the entity can set a preference for the type of post that can be updated automatically based on learned behavior by the neural network component 304. For example, if a photo is taken by the entity or a friend of the entity, then the photo can be automatically posted to the entity's appropriate social media account with an automatically generated caption. The automatically generated caption can be based on a previously generated caption by the entity for an activity posted from a previous event. For example, if the neural network component 304 observes that a previous picture was posted by a friend (e.g., named John) of the entity, comprising the entity, John, and a bicycle, wherein the post comprises the text, "cycling with John", then the neural network component 304 can apply the same or similar text to any new pictures that comprise the entity, John, and the bicycle. Therefore, the new pictures and the applied text can then be used to update the entity's social media profile without the entity having to update the profile itself.

The neural network component 304 can also learn and update posts based on daily activities (e.g., working out, sleeping, eating, etc.) associated with the entity. The daily activities can be received by the neural network component 304 to generate baseline data for the entity. For example, daily activity data of the entity can be received from other electronic media, such as calendar entries on the mobile device 110, television viewing, email usage, text usage, phone calls, etc. Additionally, the neural network component 304 can prompt the entity for missing and/or uncategorized data. For example, the neural network component 304 can prompt the entity to validate (e.g., via the validation component 204) that a calendar entry actually belongs to the entity and not a family member of the entity. Alternatively, the neural network component 304 can prompt the entity to validate that a specific email is associated with the entity's workout regimen and not the entity's competitive recreation regimen.

A support vector machine (SVM) is an example of a classifier that can be employed. The SVM can operate by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, for example, naïve Bayes, Bayesian networks, decision trees, fuzzy logic models, and probabilistic classification models providing different patterns of independence can be employed. Classification as used herein also may be inclusive of statistical regression that is utilized to develop models of priority.

The disclosed aspects can employ classifiers that are explicitly trained (e.g., via generic training data) as well as implicitly trained (e.g., via observing profile updates as it relates to the triggering events). For example, SVMs can be configured via a learning or training phase within a classifier constructor and feature selection module. Thus, the classifier(s) can be used to automatically learn and perform a number of functions, including but not limited to predicting an activity, calculating a probability of the predicted activity, updating a social media profile, and so forth. The criteria can include, but is not limited to, predefined values, contribution attenuation tables or other parameters, preferences and/or policies, and so on.

In another embodiment, the analysis component 306 can monitor and analyze a nearby entity's social media post to screen for any data associated with another entity. For example, if a first entity is tagged in a social media post of a second entity, wherein the social media post comprises text related to a specific activity, then the activity identification component 102 can use this additional information in conjunction with the received sensor data to determine if the first entity is actually partaking in the activity. Additionally, the analysis component 306 can determine which social media feed to update. For example, an activity that is appropriate for a more casual social media website (e.g., Facebook) for an entity, may not be appropriate for a professional social media website (e.g., LinkedIn) for the entity. Therefore, depending on rules set by the entity, certain updates can be reserved or restricted to certain types of social media platforms. For example, the entity may set a rule that says any photos of the entity with a drink of any type shall be reserved for the entity's more casual social media (e.g., Facebook) to prevent the perception that the entity is having an alcoholic beverage from appearing on the entity's professional social media website. The entity can also set additional criteria for not allowing an automated post based on location (e.g., work, beach, bar, etc.), proximity to a type of location (e.g., residential, business, park, restaurants, etc.), a nearby entity (e.g., adult, kid, etc.), an activity (e.g., concert, conference, etc.), and/or a time (e.g., day, night, morning, evening, night, work hours, etc.). For example, one rule could restrict any photos taken at a concert from being posted during work hours.

Figure 4:
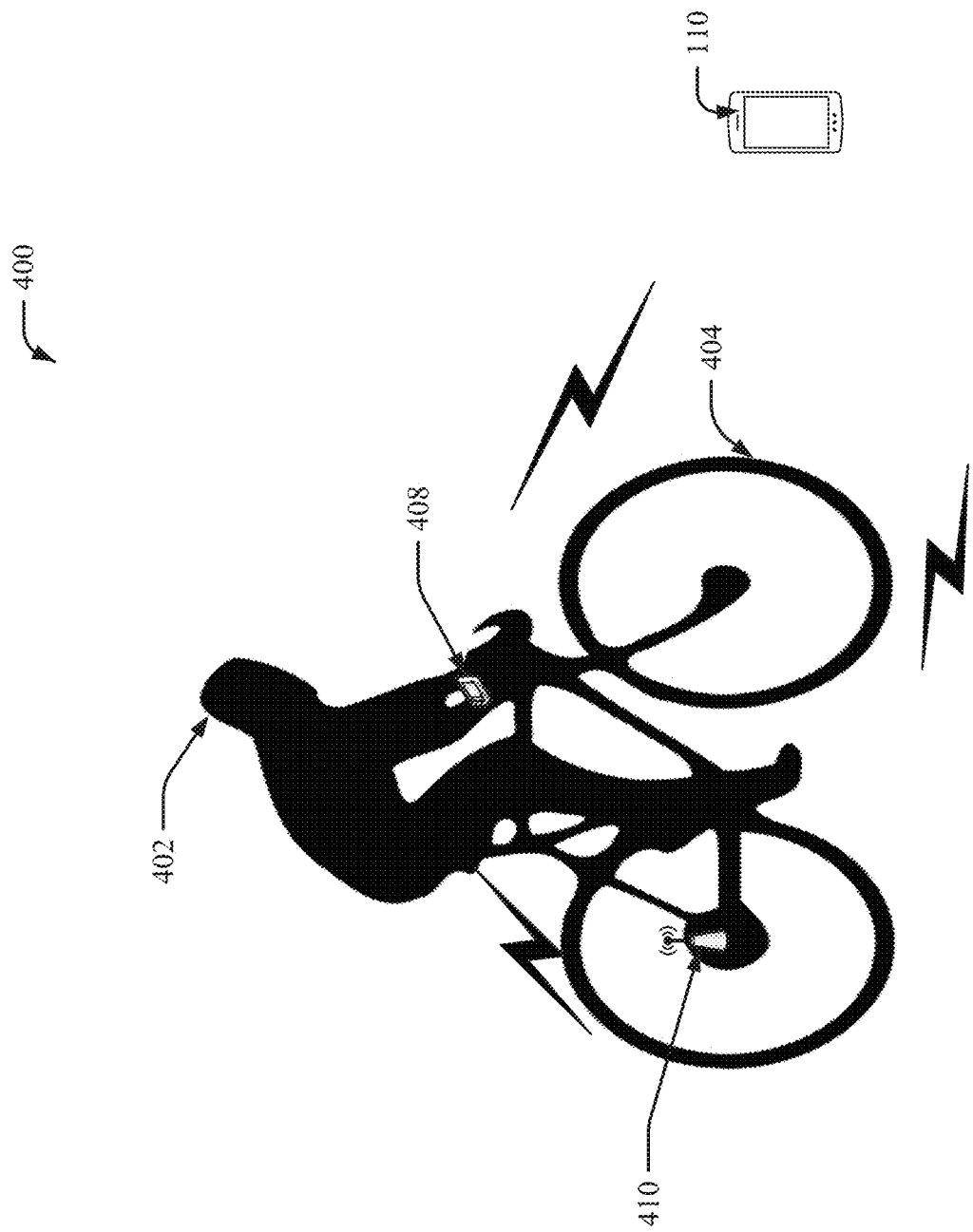
FIG. 4 illustrates an example, non-limiting system that facilitates automatically updating social media profiles based on sensor data in accordance with one or more embodiments described herein.

FIG. 4 illustrates an example, non-limiting system that facilitates automatically updating social media profiles based on sensor data in accordance with one or more embodiments described herein. Repetitive description of like elements employed in other embodiments described herein is omitted for sake of brevity.

FIG. 4 depicts an entity 402 riding a bicycle 404. As depicted in FIG. 4, there are three possible points for sensor data: a velocity sensor 410, a heart monitor sensor 408, and a mobile device with GPS tracking and camera capabilities. It should be noted that although FIG. 4 depicts three separate devices, in some embodiments, one device can comprise all three sensors and/or additional sensors. It should also be noted that one device can act as the curator for all the sensor data. For instance, the velocity sensor 410, and the heart monitor sensor 408 can both send their respective sensor data to the mobile device 110, and the mobile device can send the velocity sensor data, the heart monitor sensor, GPS data, and picture data to the profile modification component 100, 200, 300. Alternatively, each sensor can send its own data to the profile modification component 100, 200, 300.

Based on the sensor data received from the sensor devices, the activity identification component 102 of the profile modification component 100 can predict the activity of the entity 402. Various thresholds can be set by the activity identification component 102 to restrict irrelevant data. For example, if the velocity sensor 410 is indicating that the bicycle 404 is moving at less than one mile per hour, then this may not be a proper indication that the bicycle 404 is actually being ridden. Thus, the activity identification component 102 can set a threshold value that the velocity sensor must indicate that the bicycle 404 is moving at greater than five miles per hour for any of the velocity sensor data to be accounted for in determining whether the entity 402 is performing the activity of bicycling. Furthermore, the more that the velocity sensor data indicates that the bicycle 404 is moving at a higher velocity, the more the velocity sensor data can be weighted for determining that the entity 402 is bicycling. The threshold values can also be set for multiple sensors in tandem. For example, the activity identification component 102 may only validate the activity of bicycling if the velocity sensor 410 indicates the bicycle is moving above five miles per hour, the heart monitor sensor 408 indicates a heart rate of ninety beats per minute or above, and the GPS of the mobile device has indicated at least a one tenth of a mile ride. A time period can also be applied such that each of those factors must be sustained for a defined period of time to identify the activity. It should be noted that any thresholds or time values can be used and that the entity 402 can predetermine what thresholds and/or time values best reflect their activities.

Figure 5:
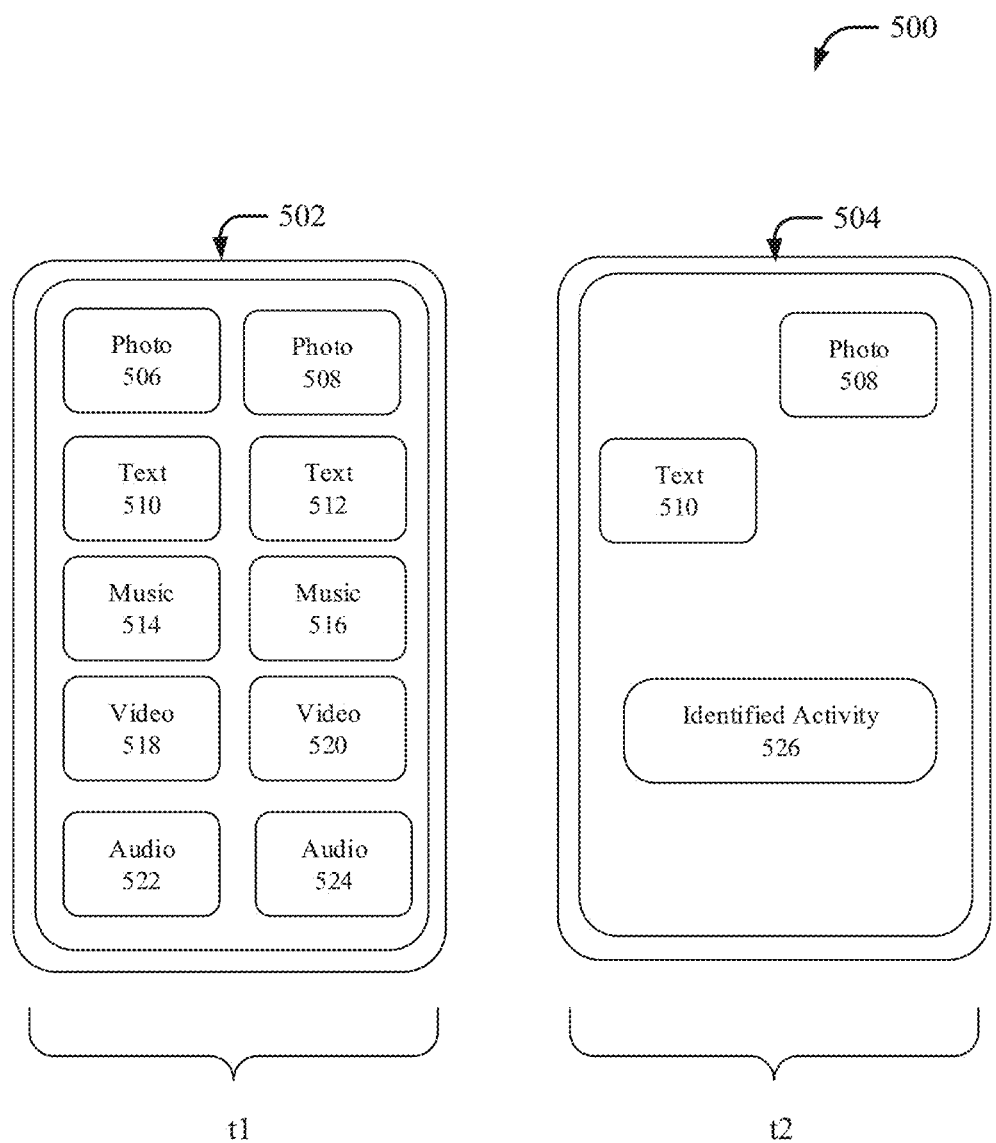
FIG. 5 illustrates an additional block diagram of example, non-limiting mobile device displays that facilitate auto-selection of data for updating a social media profile in accordance with one or more embodiments described herein.

FIG. 5 illustrates an additional block diagram of example, non-limiting mobile device displays 500 that facilitate auto-selection of data for updating a social media profile in accordance with one or more embodiments described herein. Repetitive description of like elements employed in other embodiments described herein is omitted for sake of brevity.

Once the activity of FIG. 4 is determined, the updating component 104 can then update the social media profile of the entity 402 or send a validation request (e.g., the validation component 204) to the entity 402 to approve the activity and/or the update prior to updating the social media profile. The update to the social media profile can comprise several of media including, but not limited to previously stored text 510, 512, photographs 506, 508, audio 522, 524, music 514, 516, video 518, 520, etc.

FIG. 5 depicts the possible update options from the mobile device 110 at a first time t1 and the social media profile updates based on the identified activity 526 at a second time t2. The entity 402 can associate the previously stored text 510, 512, photographs 506, 508, audio 522, 524, music 514, 516, and/or video 518, 520 with the identified activity 526, which has been predicted by the activity identification component 102. For example, the entity 402 can configure the updating component 104 to update its social media profile with the previously stored photographs 508 and the previously stored text 510 (e.g. from first time t1) data that the entity 402 has associated with the identified activity 526 (e.g., bicycling) for the second time t2 after the activity has been identified. Alternatively, the entity 402 can configure the updating component 104 to update its social media profile with current data. For example, instead of updating the social media profile with the previously stored photographs 508, the social media profile can be updated with a current photo of the entity 402 currently performing the identified activity 526 (e.g., bicycling). Determining what information to update the social media profile with can also be based on other factors. For example, if the photo data received from a third-party is indicative of the entity 402 bicycling, then the system can update the social media profile with a previously stored video 518 of the entity 402 bicycling. However, if velocity data indicative of bicycling is received from the velocity sensor 410, then the system can update the social media profile with current GPS data taken from the entity's 402 mobile device 110.

Figure 6:
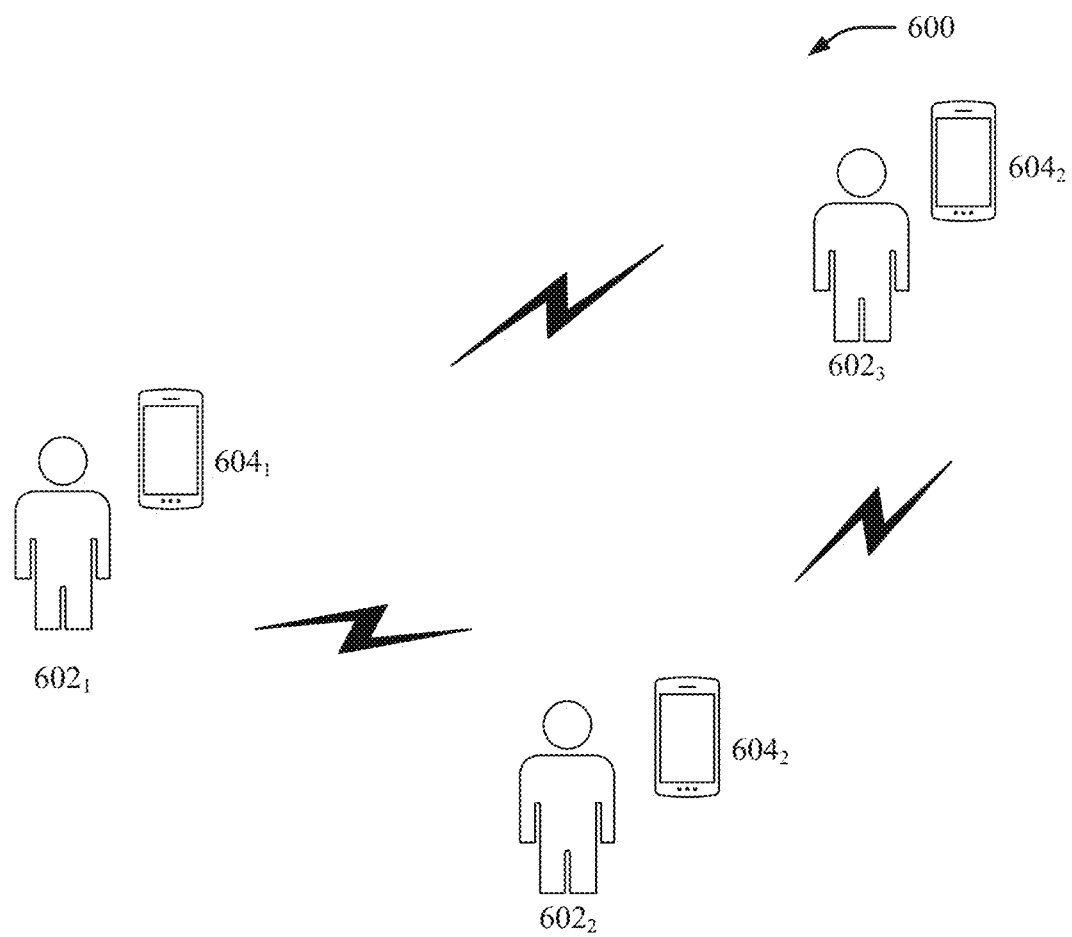
FIG. 6 illustrates an example, non-limiting system that facilitates automatically updating social media profiles based on other entity data in accordance with one or more embodiments described herein.

FIG. 6 illustrates an example, non-limiting system 600 that facilitates automatically updating social media profiles based on other entity data in accordance with one or more embodiments described herein. Repetitive description of like elements employed in other embodiments described herein is omitted for sake of brevity.

FIG. 6 depicts another embodiment wherein multiple mobile devices $110_1$, $110_2$, $110_3$ are associated with multiple entities $402_1$, $402_2$, $402_3$, respectively. However, photographs taken by entities $402_2$, $402_3$ can be used to update a social media profile of the entity $402_1$ whether the entity $402_1$ possesses its mobile devices or not. For example, facial image recognition technology can recognize the entity $402_1$ has had a photograph taken by another entity's $402_2$ mobile device $110_3$. GPS data can also be applied to the photograph so that a location of the entity $402_1$ is also known. In the case where the entity $402_1$ does not possess its mobile device $110_1$ (not shown) or its mobile device $110_1$ is not in use, the photo can be sent to a mobile network to be provisioned based on predefined rules of the profile modification component 200, wherein the identified activity is that the entity $402_1$ is at the location. Based on a predefined rule set by the entity $402_1$, the photograph can automatically update the social media profile of the entity $402_1$. Alternatively, if the entity $402_1$ is using its mobile device $110_1$, the photo can be sent to the mobile device $110_1$, wherein the validation component 204 can prompt the entity $402_1$ to approve the photograph and/or approve an update of the entity's $402_1$ location being updated on its social media profile. Additionally, the probability of the entity $402_1$ being at the location can be increased by additional photographs and location data being provided by another mobile device $110_3$ utilized by another entity $402_3$.

In an additional embodiment, other entities $402_2$, $402_3$ can have pre-approved social media profiles and/or be a part of a trusted social circle (e.g., family, friends, colleagues, care providers, etc.) allowed to provide profile update data for the entity $402_1$. For example, the entity $402_1$ can validate (e.g., via the validation component 204) other entities $402_2$, $402_3$, mobile devices $110_2$, $110_3$ of the other entities $402_2$, $402_3$, and/or social media profiles of the other entities $402_2$, $402_3$ to allow data curated by the other entities $402_2$, $402_3$ to update the social media profile of the entity $402_1$. Additionally, the trusted social circle can be social media platform-specific. For example, because an entity's professional social media platform can comprise friends that are not necessarily listed as friends on the entity's more casual social media platform (e.g., Facebook), specific entities can be validated based on which social media platform in which they participate.

Figure 7:
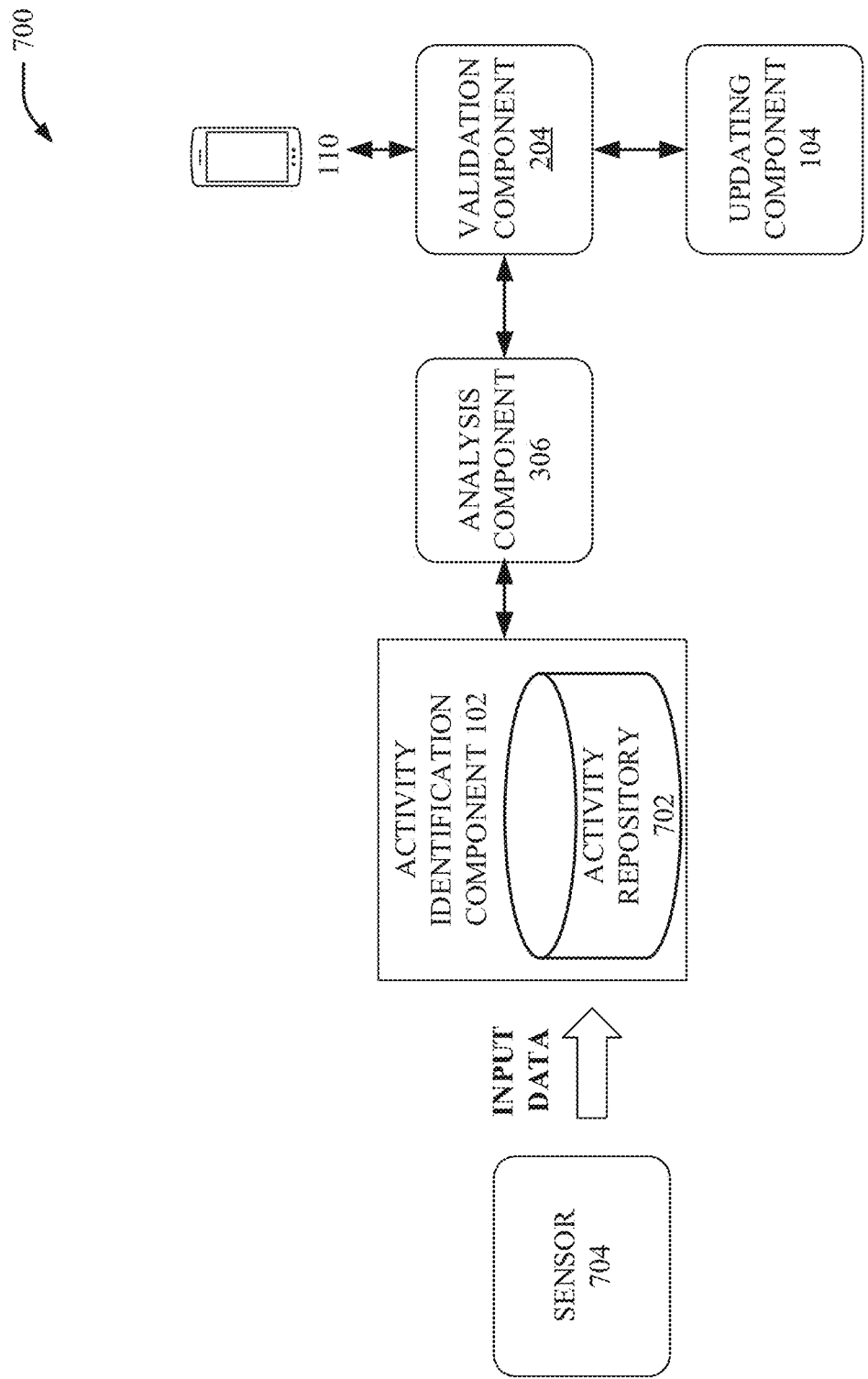
FIG. 7 illustrates a block diagram of an example, non-limiting system that facilitates automatically collecting data and updating social media profiles based on sensor data in accordance with one or more embodiments described herein.

FIG. 7 illustrates a block diagram of an example, non-limiting system that facilitates automatically collecting data and updating social media profiles based on sensor data in accordance with one or more embodiments described herein. Repetitive description of like elements employed in other embodiments described herein is omitted for sake of brevity.

In another embodiment, FIG. 7 depicts a system 700 that comprises a sensor 704, the activity identification component 102, and activity repository 702, an analysis component 306, a validation component 204, an updating component 104, and a mobile device 110, which can be electrically and/or communicatively coupled to one another in various embodiments. The activity identification component 102 can receive sensor data from the sensor 704 as an input. For example, optical sensors, heart rate sensors, gyroscopes, accelerometers, GPS sensors, microphone sensors, audio sensors, light sensors, infrared sensors, and/or RFID sensors can send sensor data to the activity identification component. The analysis component 306 can analyze the sensor data to predict a particular activity, resulting in an activity prediction. For example, the analysis of the sensor data can comprise determining which sensor the sensor data came from, determining whether the sensor data is accurate based on aggregate sensor data, and/or determining if the sensor data is associated with another entity $402_2$.

The activity prediction can then be sent to the validation component 204. The validation component 204 can prompt the entity 402 (via the mobile device 110) to confirm the activity and/or confirm whether the social media profile of the entity 402 should be updated with the confirmed activity data via the updating component 104. For example, if the analysis component 306 predicts that the entity 402 is swimming, then the validation component 204 can prompt the entity 402 to validate that the entity 402 is swimming. If the entity 402 validates the activity and/or if the entity allows the updating component 104 to update the social media profile, then the confirmed activity can then be stored in the activity repository 702. Consequently, when the same or similar sensor data is received from the sensor 704 during a future iteration, based on rules set by the entity 402, the updating component 104 can bypass the validation via the validation component 204.

Figure 8:
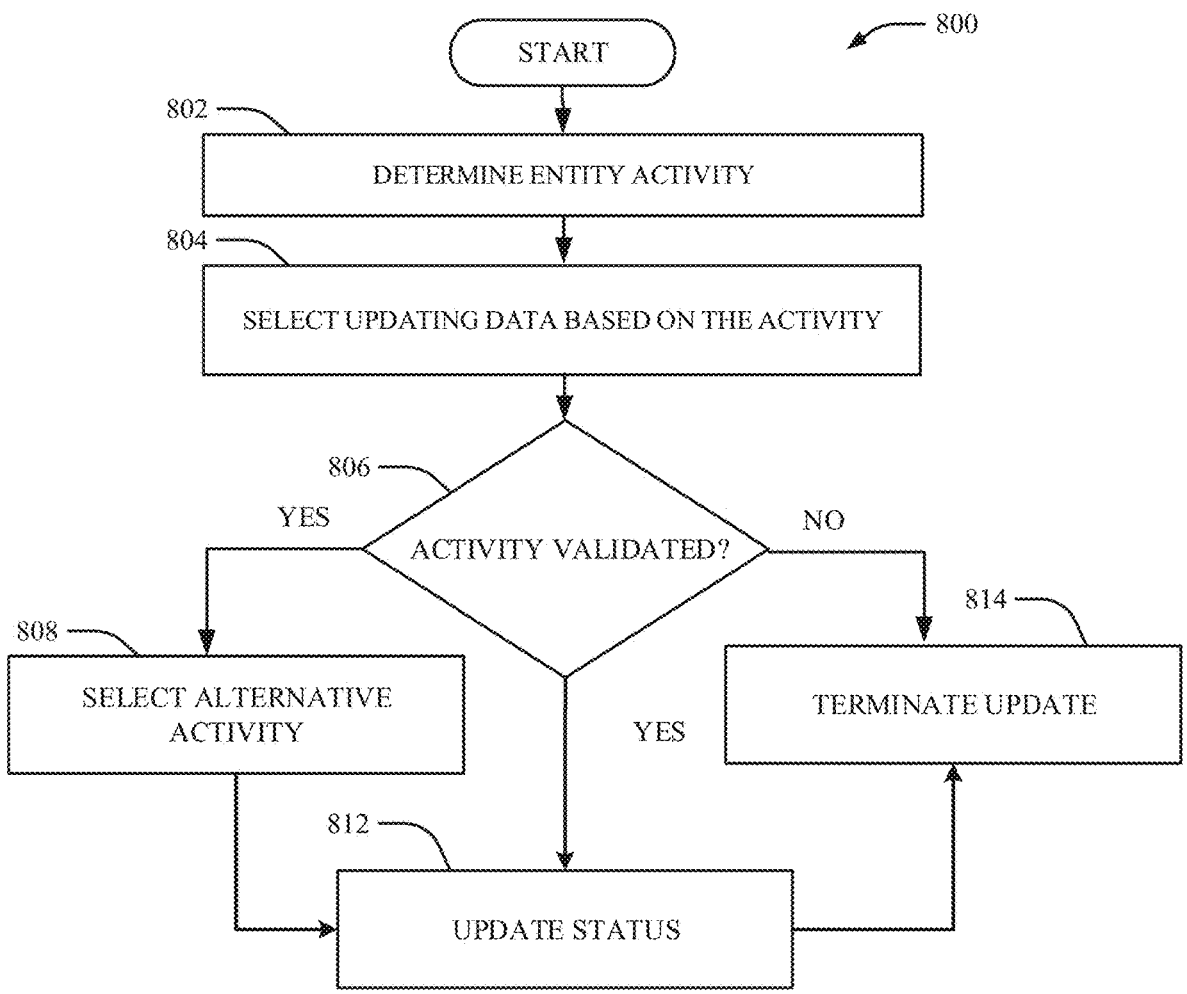
FIG. 8 illustrates a flow diagram of an example, non-limiting system that facilitates automatically collecting data and updating social media profiles based on sensor data in accordance with one or more embodiments described herein.

FIG. 8 illustrates a flow diagram of an example, non-limiting computer-implemented method that facilitates automatically collecting data and updating social media profiles based on sensor data in accordance with one or more embodiments described herein. Repetitive description of like elements employed in other embodiments described herein is omitted for sake of brevity.

The system 800 can determine entity activity (e.g., via the activity identification component 102) at element 802 based on sensor data received by the profile modification component 100, 200, 300. For example, facial image recognition sensors can send sensor data to the activity identification component 102. Based on the sensor data, the profile modification component 100, 200, 300 can identify data to update an entity's profile. Consequently, the system 800 can select updating data (e.g., via the updating component 104) based on the activity at element 804. At element 806, the system 800 can determine if the activity is validated (e.g., via the validation component 204). The validation component 204 can prompt the entity 402 to validate that the entity 402 is participating in or has recently participated in the activity. For example, the entity 402 can validate that the entity 402 is rock climbing, and allow the updating component 104 to update the social media profile. In some embodiments, the activity can be pre-validated. For instance, if the entity 402 knows that he/she is going rock climbing, the entity 402 can pre-validate any sensor data indicative of the entity 402 participating in rock climbing. Thus, if the activity is pre-validated by the entity 402, then the system 800 can update the status (e.g., via the updating component 104) of the entity's 402 social media profile at element 812 and terminate the update at element 814. However, if the activity is not pre-validated, then the system 800 can prompt the entity 402 to select an alternative activity at element 808 to update (e.g., via the updating component 104) the entity's profile status at element 812 prior to terminating the update at element 814. Alternatively, if the activity is not validated, then the system 800 can simply terminate the update at element 814.

Figure 9:
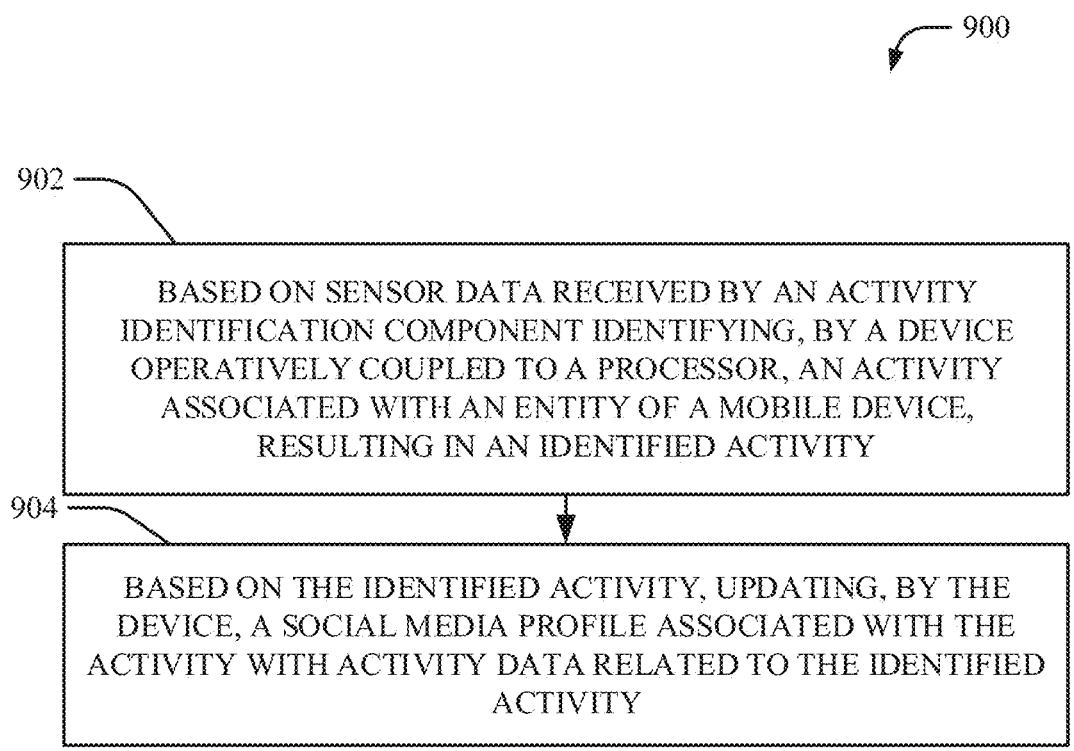
FIG. 9 illustrates a flow diagram of an example, non-limiting computer-implemented method that facilitates automatically collecting data and updating social media profiles based on sensor data in accordance with one or more embodiments described herein.

FIG. 9 illustrates a flow diagram 900 of an example, non-limiting computer-implemented method that facilitates automatically collecting data and updating social media profiles based on sensor data in accordance with one or more embodiments described herein. Repetitive description of like elements employed in other embodiments described herein is omitted for sake of brevity.

At element 902, the flow diagram 900 can comprise identifying (e.g., via the activity identification component 102), by a device operatively coupled to a processor, an activity associated with an entity 402 of a mobile device 110, resulting in an identified activity based on sensor data (e.g., received from the sensor component 202) received by an activity identification component 102. For example, GPS sensors can send GPS sensor data to the activity identification component 102 indicative of the entity 402 transitioning from a first location to a second location. Based on the sensor data, the profile modification component 100, 200, 300 can identify data to update an entity's profile, namely that the entity 402 is transitioning from the first location to the second location. Additionally, at element 904, the flow diagram 900 can comprise updating (e.g., via the updating component 104), by the device, a social media profile associated with the activity with activity data related to the identified activity based on the identified activity. Consequently, the entity's profile can be updated with such transition data.

Figure 10:
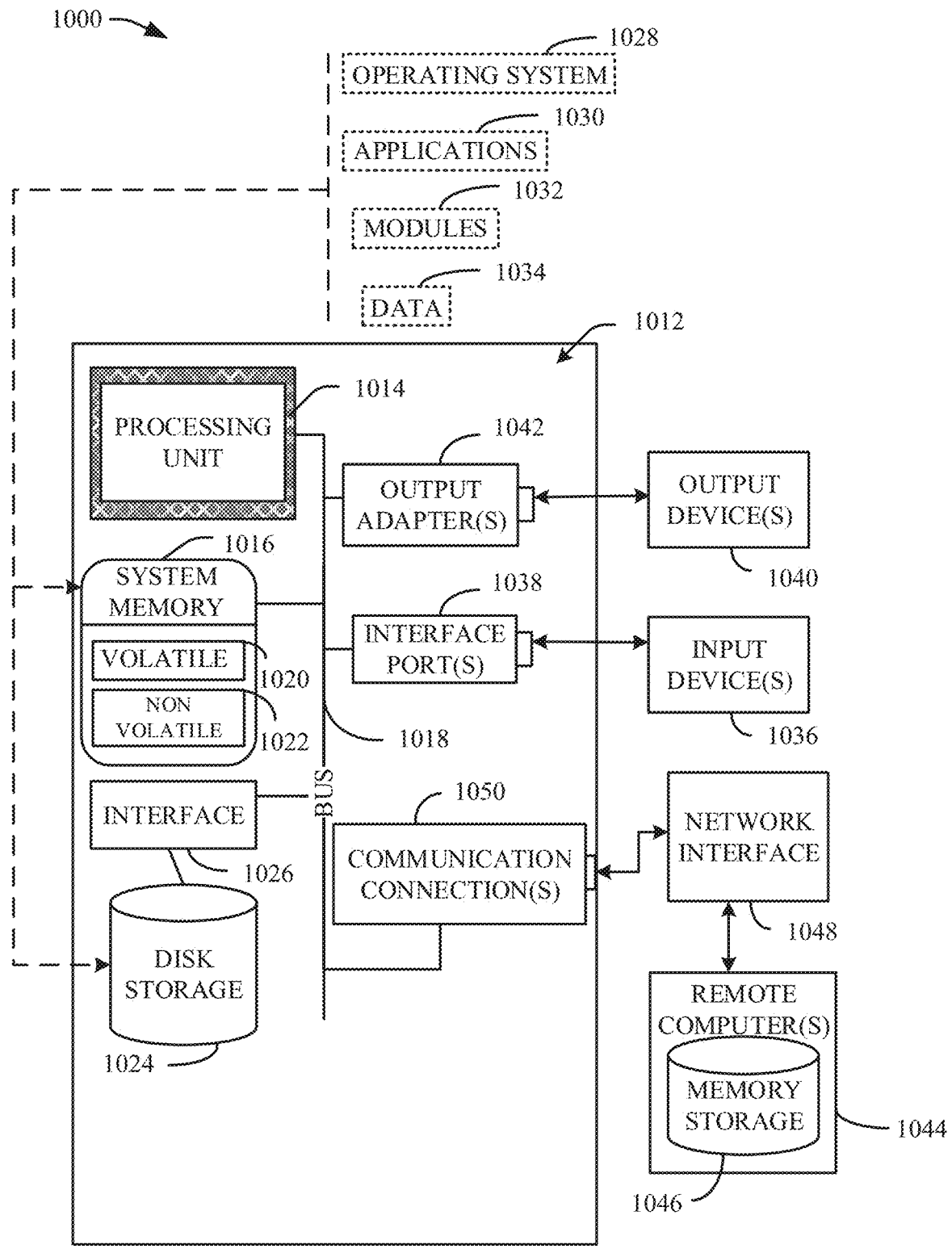
FIG. 10 illustrates a block diagram of an example, non-limiting operating environment in which one or more embodiments described herein can be facilitated.

In order to provide a context for the various aspects of the disclosed subject matter, FIG. 10 as well as the following discussion is intended to provide a general description of a suitable environment in which the various aspects of the disclosed subject matter can be implemented. FIG. 10 illustrates a block diagram of an example, non-limiting operating environment in which one or more embodiments described herein can be facilitated. With reference to FIG. 10, a suitable operating environment 1000 for implementing various aspects of this disclosure can also include a computer 1012. The computer 1012 can also include a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface is typically used, such as interface 1026. FIG. 10 also depicts software that acts as an intermediary between users and the basic computer resources described in the suitable operating environment 1000. Such software can also include, for example, an operating system 1028. Operating system 1028, which can be stored on disk storage 1024, acts to control and allocate resources of the computer 1012.

System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

The present disclosure may be a system, a method, an apparatus and/or a computer program product at any possible technical detail level of integration. The computer program product can include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DR-RAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components; and
   a processor that executes the computer executable components stored in the memory, wherein the computer executable components comprise:
   an activity identification component that:
     based on:
       selected sensor data received by the activity identification component; and
       qualifying data employed as baseline data to delineate an activity from a second activity, wherein the activity and the second activity are both within a scope of possible activities based on the selected sensor data, identifies the activity as being associated with an entity of a mobile device, resulting in an identified activity, wherein the selected sensor data is selected as relevant from a set of sensor data based on comparing numerical values of the set of sensor data to parameter types and respective parameter thresholds for the parameter types and identifying the selected sensor data as meeting the respective parameter thresholds for the parameter types, and wherein the parameter types differ from one another;

a validation component that:
prompts the entity, wherein the prompt requests confirmation of whether the identified activity is correct and requests confirmation of whether the entity would like for a social media profile associated with the entity to be updated with the identified activity; and
receives validation data comprising a qualification changing the identified activity to the second activity, the identified activity being distinct from the second activity, wherein receipt of the validation data is in response to:
prompting the entity to confirm whether the identified activity is correct or prompting the entity to confirm that the second activity is correct notwithstanding the selected sensor data has previously been associated with the identified activity; and
a determination that the selected sensor data and the qualification should be associated with the second activity and should not be associated with the identified activity for current and future instances of detection of the selected sensor data;
an updating component that:
based on the received validation data comprising the qualification and based on the selected sensor data, updates, with activity data related to the second activity, a social media profile for the entity; and
a neural network component that learns and automatically updates, without entity intervention, posts to the social media profile associated with the entity, wherein the neural network component learns and automatically updates the social media profile based on:
learned past and current daily activities of the entity received from other electronic media of the entity, wherein the other electronic media comprises calendar entries on the other electronic media; and
a determination that the calendar entries belong to the entity and not a family member associated with the entity.

2. The system of claim 1, wherein the set of sensor data comprises biometric sensor data, wherein the identified activity and the second activity are each a physical activity and wherein the biometric sensor data is utilized to determine the physical activity being performed by the entity, and wherein the identified activity comprises running and the second activity comprises jogging, and wherein the neural network component also learns and automatically updates, without entity intervention, posts to the social media profile associated with the entity, wherein the neural network component learns and automatically updates the social media profile based on:
an identified email message of the entity or an identified text message of the entity; and
if the identified email message of the entity is employed, a determination that the identified email message of the entity is associated with a first category of email message of the entity and not a second category of email message of the entity.

3. The system of claim 1, wherein the computer executable components further comprise:
one or more sensor components that:
generate the set of sensor data; and
transmit the set of sensor data to the activity identification component for analysis by the activity identification component, and wherein the first category of email of the entity is a workout regimen of the entity and wherein the second category of email of the entity is a competitive recreation regimen of the entity.

4. The system of claim 3, wherein an accuracy of the identified activity increases as a number of the one or more sensors increases from a first number of the one or more sensors to a second number of the one or more sensors.

5. The system of claim 1, wherein the mobile device is a first mobile device, wherein the set of sensor data is first sensor data, and wherein a set of second sensor data received from a second mobile device is utilized to identify the identified activity.

6. The system of claim 1, wherein the activity identification component comprises a global positioning system capable of generating global positioning system data to be utilized in identifying the activity.

7. The system of claim 1, wherein the updating component selects a picture to update the social media profile based on the second activity.

8. The system of claim 1, wherein the updating component selects a to update the social media profile based on the second activity.

9. A computer program product that facilitates automated profile updates, the computer program product comprising a computer readable storage medium having program instructions embodied therewith, the program instructions executable by a processor to cause the processor to:
in response to identification of sensor data received by an activity identification component and qualifying data employed as baseline data to delineate an activity from a second activity wherein the activity and the second activity are both within a scope of possible activities based on the selected sensor data:
identify an activity associated with an entity of a mobile device, resulting in an identified activity, wherein the sensor data comprises a picture of the entity taken by the mobile device;
based on the identified activity, update a social media profile associated with the activity with activity data related to the identified activity, wherein the activity data with which the social media profile is updated comprises the picture of the entity taken by the mobile device in determining the identified activity;
prompt the entity to confirm whether the identified activity is correct; and
receive validation data comprising a validation of the identified activity, wherein receipt of the validation data is in response to prompting the entity to confirm whether the identified activity is correct or that the second activity is correct notwithstanding the selected sensor data has previously been associated with the identified activity; and
in response to an absence of sensor data:
determine a probability associated with an activity determination being correct based on tagged or partitioned data;
generate activity identification data based on learned behavior associated with past activities received from electronic media;
update a post to a social media profile associated with the activity identification data based on the learned behavior and based on determination that updating will not violate a rule of a plurality of rules set by the entity, wherein the plurality of rules comprise restrictions on not allowing automated posts if the entity is at or within a defined proximity to a particular type of location, during defined hours, nearby a second identified entity or if the activity identification data indicates the identified activity is of a certain type, wherein the social media profile is one of a plurality of social media profiles associated with the entity, and wherein the plurality of social media profiles comprises a casual social media profile or a professional social media profile; and determine to which social media profile to update, wherein the determination of which social media profile to update is based on whether the activity data indicates that the activity is appropriate for a casual social media website for the entity or is appropriate for a professional social media website for the entity, a determination that posting will not violate the plurality of rules set by the entity.

10. The computer program product of claim 9, wherein the sensor data further comprises biometric sensor data, and wherein the biometric sensor data is utilized to determine a physical activity being performed by the entity.

11. The computer program product of claim 9, wherein the program instructions are further executable by the processor to cause the processor to:

generate the sensor data; and transmit the sensor data to the activity identification component for analysis by the activity identification component.

12. The computer program product of claim 11, wherein an accuracy of the identified activity increases as a number of the one or more sensors increases from a first number of the one or more sensors to a second number of the one or more sensors.

13. The computer program product of claim 9, wherein the mobile device is a first mobile device, wherein the sensor data is first sensor data, wherein second sensor data crowdsourced from a set of mobile devices distinct from the mobile device and the first sensor data and the second sensor data is utilized to identify the identified activity.

14. The computer program product of claim 9, wherein the second identified entity is a child or an identified adult.

15. A computer-implemented method, comprising:

based on sensor data received by an activity identification component and qualifying data employed as baseline data to delineate an activity from a second activity wherein the activity and the second activity are both within a scope of possible activities based on the selected sensor data:

identifying, by a device operatively coupled to a processor, an activity associated with an entity of a mobile device, resulting in an identified activity, wherein the sensor data is crowdsourced data from one or more other mobile devices associated with entities other than the entity and wherein the one or more other mobile devices are distinct from the mobile device, and wherein the sensor data comprises data processed via facial recognition software at the mobile device or at a mobile network that identifies the entity;

determining, by the device, a location of the entity and monitoring, by the device, text of social media posts of one of the other entities that is nearby the entity;

determining, by the device, that the entity is tagged in one of the social media posts of one of the other entities that is nearby the entity and, based on the text of the social media post of one of the other entities that is nearby the entity, that the identified activity is the same activity as the activity tagged by the one of the other entities;

based on the identified activity and based on the social media post of one of the other entities that is nearby the entity providing content that confirms the identified activity is correct, updating, by the device, a social media profile associated with the activity with activity data related to the identified activity;

prompting, by the device, the entity to confirm whether the identified activity is correct; and receiving, by the device, validation data comprising a validation of the identified activity, wherein receipt of the validation data is in response to prompting the entity to confirm whether the identified activity is correct or the second activity is correct notwithstanding the selected sensor data has previously been associated with the identified activity; and based on an absence of sensor data:

determining a probability associated with an activity determination being correct based on tagged or partitioned data;

generating activity identification data based on learned behavior associated with past activities received from electronic media; and updating a post to a social media profile associated with the activity identification data based on the learned behavior.

16. The computer-implemented method of claim 15, wherein the sensor data further comprises biometric sensor data, and wherein the biometric sensor data is utilized to determine a physical activity being performed by the entity.

17. The computer-implemented method of claim 15, wherein the mobile device is a first mobile device, wherein the sensor data is first sensor data, and wherein second sensor data received from a second mobile device of the one or more other mobile devices is utilized to identify the identified activity.

18. The computer-implemented method of claim 15, wherein the activity identification component comprises a global positioning system capable of generating global positioning system data to be utilized in identifying the activity.

\* \* \* \* \*